US010241180B2

United States Patent
Markl et al.

(10) Patent No.: US 10,241,180 B2
(45) Date of Patent: Mar. 26, 2019

(54) SYSTEM AND METHOD FOR MAPPING AND QUANTIFYING IN-VIVO BLOOD FLOW STASIS

(71) Applicant: Northwestern University, Evanston, IL (US)

(72) Inventors: Michael Markl, Chicago, IL (US); Jeffrey J. Goldberger, Skokie, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/546,770

(22) PCT Filed: Jan. 29, 2016

(86) PCT No.: PCT/US2016/015639
§ 371 (c)(1),
(2) Date: Jul. 27, 2017

(87) PCT Pub. No.: WO2016/123477
PCT Pub. Date: Aug. 4, 2016

(65) Prior Publication Data
US 2018/0031662 A1 Feb. 1, 2018

Related U.S. Application Data

(60) Provisional application No. 62/109,909, filed on Jan. 30, 2015.

(51) Int. Cl.
*G06K 9/00* (2006.01)
*G01R 33/563* (2006.01)
(Continued)

(52) U.S. Cl.
CPC ...... *G01R 33/56325* (2013.01); *A61B 5/0263* (2013.01); *A61B 5/055* (2013.01);
(Continued)

(58) Field of Classification Search
None
See application file for complete search history.

(56) References Cited

U.S. PATENT DOCUMENTS 5,515,852 A * 5/1996 Karp .................. G01N 29/38
600/443
5,900,731 A 5/1999 Henkelman et al.
(Continued)

OTHER PUBLICATIONS

Asinger Rw, et al. Pathophysiologic correlates of thromboembolism in nonvalvular atrial fibrillation: Ii. Dense spontaneous echocardiographic contrast (the stroke prevention in atrial fibrillation [spaf-iii] study). J Am Soc Echocardiogr. 1999;12:1088-1096.
(Continued)

*Primary Examiner* — Vikkram Bali
(74) *Attorney, Agent, or Firm* — Quarles & Brady LLP (57) ABSTRACT

Described here are systems and methods for producing an image that depicts blood flow stasis using magnetic resonance imaging (MRI), Doppler echocardiography, or other medical instruments for measuring flow velocities in a human body. A time series of three-dimensional (3D) image volumes is provided, where this time series of 3D image volumes contains flow velocity information at voxel locations in a 3D volume in a subject. One or more regions-of-interest are then segmented from the 3D image volumes. For each voxel in the regions-of-interest, velocity magnitudes are calculated. Using the velocity magnitudes, a flow stasis volume is produced by computing a relative stasis value for each voxel location in the corresponding region-of-interest. This flow stasis volume can be provided as a 3D flow stasis image, or a flow stasis map can be produced by projecting the flow stasis volume onto a two-dimensional (2D) plane.

9 Claims, 5 Drawing Sheets

(51) Int. Cl.

| | |
|---|---|
| G01R 33/56 | (2006.01) |
| G06T 7/62 | (2017.01) |
| G06T 7/11 | (2017.01) |
| G06T 7/174 | (2017.01) |
| A61B 5/026 | (2006.01) |
| A61B 5/055 | (2006.01) |
| G06T 7/00 | (2017.01) |
| G06T 7/20 | (2017.01) |
| G06T 11/00 | (2006.01) |

(52) U.S. Cl.
CPC ........ *G01R 33/5608* (2013.01); *G06T 7/0016* (2013.01); *G06T 7/11* (2017.01); *G06T 7/174* (2017.01); *G06T 7/20* (2013.01); *G06T 7/62* (2017.01); *G06T 11/008* (2013.01); *A61B 2576/02* (2013.01); *G06T 2207/10088* (2013.01); *G06T 2207/10136* (2013.01); *G06T 2207/30048* (2013.01); *G06T 2207/30104* (2013.01)

(56) References Cited

U.S. PATENT DOCUMENTS

| | | | | |
|---|---|---|---|---|
| 2004/0113613 | A1* | 6/2004 | Markl | G01R 33/5613 324/306 |
| 2006/0155187 | A1 | 7/2006 | Zhao et al. | |
| 2009/0088626 | A1 | 4/2009 | Sutton et al. | |
| 2009/0116711 | A1 | 5/2009 | Larson et al. | |
| 2010/0094122 | A1* | 4/2010 | Kiraly | A61B 5/021 600/419 |
| 2011/0175608 | A1* | 7/2011 | McNeal | G01R 33/56316 324/306 |
| 2011/0224962 | A1* | 9/2011 | Goldberger | G06T 7/0012 703/11 |
| 2011/0230756 | A1* | 9/2011 | Axel Odeen | G01R 33/5608 600/419 |
| 2013/0137967 | A1* | 5/2013 | Zhang | A61B 5/055 600/413 |

OTHER PUBLICATIONS

Bock J, et al. Optimized pre-processing of time-resolved 2d and 3d phase contrast mri data. Proceedings of the 15th Annual Meeting of ISMRM, Berlin, Germany. 2007:3138.

Bock J, Frydrychowicz A, Stalder Af, et al. 4d phase contrast mri at 3 t: Effect of standard and blood-pool contrast agents on snr, pc-mra, and blood flow visualization. Magn Reson Med. 2010;63:330-338.

Chugh Ss, et al. Worldwide epidemiology of atrial fibrillation: A global burden of disease 2010 study. Circulation. 2013.

Di Biase L, et al. Does the left atrial appendage morphology correlate with the risk of stroke in patients with atrial fibrillation? Results from a multicenter study. J Am Coll Cardiol. 2012;60:531-538.

Dumoulin Cl. Phase contrast mr angiography techniques. Magn Reson Imaging Clin N. Am. 1995;3:399-411.

Ebbers T, et al. Noninvasive measurement of time-varying three-dimensional relative pressure fields within the human heart. J Biomech Eng. 2002;124:288-293.

Eriksson J, Carlhall Cj, Dyverfeldt P, et al. Semi-automatic quantification of 4d left ventricular blood flow. J Cardiovasc Magn Reson. 2010;12:9.

Fluckiger Ju, et al. Left atrial flow velocity distribution and flow coherence using four-dimensional flow mri: A pilot study investigating the impact of age and pre- and postintervention atrial fibrillation on atrial hemodynamics. J Magn Reson Imaging. 2013;38:580-587.

Foll D, et al. Age, gender, blood pressure, and ventricular geometry influence normal 3d blood flow characteristics in the left heart. Eur Heart J Cardiovasc Imaging. 2013;14:366-373.

Francois Cj, et al. 4d cardiovascular magnetic resonance velocity mapping of alterations of right heart flow patterns and main pulmonary artery hemodynamics in tetralogy of fallot. J Cardiovasc Magn Reson. 2012;14:16.

Frydrychowicz A, et al. Four-dimensional phase contrast magnetic resonance angiography: Potential clinical applications. European journal of radiology. 2011.

Fuster V, et al. 2011 accf/aha/hrs focused updates incorporated into the acc/aha/esc 2006 guidelines for the management of patients with atrial fibrillation: A report of the american college of cardiology foundation/american heart association task force on practice guidelines. Circulation. 2011;123:e269-367.

Fyrenius A, et al. Three dimensional flow in the human left atrium. Heart. 2001;86:448-455.

Goldman Me, et al. Pathophysiologic correlates of thromboembolism in nonvalvular atrial fibrillation: I. Reduced flow velocity in the left atrial appendage (the stroke prevention in atrial fibrillation [spaf-iii] study). J Am Soc Echocardiogr. 1999;12:1080-1087.

Handke M, et al. Left atrial appendage flow velocity as a quantitative surrogate parameter for thromboembolic risk: Determinants and relationship to spontaneous echocontrast and thrombus formation—a transesophageal echocardiographic study in 500 patients with cerebral ischemia. J Am Soc Echocardiogr. 2005;18:1366-1372.

Kilner Pj, et al. Asymmetric redirection of flow through the heart. Nature. 2000;404:759-761.

Markl M, et al. Comprehensive 4d velocity mapping of the heart and great vessels by cardiovascular magnetic resonance. J Cardiovasc Magn Reson. 2011;13:7.

Markl, M. et al., Left atrial 4-dimensional flow magnetic resonance imaging: Stasis and velocity mapping in patients with atrial fibrillation, Investigate Radiology, 2015, 51(3):147-154.

Markl M, Fluckiger Ju, Lee Dc, et al. Velocity quantification by electrocardiography-gated phase contrast magnetic resonance imaging in patients with cardiac arrhythmia: A simulation study based on real time transesophageal echocardiography data in atrial fibrillation. J Comput Assist Tomogr. 2015 published online.

Pollick C, et al. Assessment of left atrial appendage function by transesophageal echocardiography. Implications for the development of thrombus. Circulation. 1991;84:223-231.

Roes Sd, et al. Flow assessment through four heart valves simultaneously using 3-dimensional 3-directional velocity-encoded magnetic resonance imaging with retrospective valve tracking in healthy volunteers and patients with valvular regurgitation. Investigative radiology. 2009;44:669-675.

Suwa K, Saitoh T, Takehara Y, et al. Characteristics of intra-left atrial flow dynamics and factors affecting formation of the vortex flow. Circ J. 2014.

Uribe S, Beerbaum P, Sorensen Ts, et al. Four-dimensional (4d) flow of the whole heart and great vessels using real-time respiratory self-gating. Magn Reson Med. 2009;62:984-992.

Valverde I, et al. 4d phase-contrast flow cardiovascular magnetic resonance: Comprehensive quantification and visualization of flow dynamics in atrial septal defect and partial anomalous pulmonary venous return. Pediatr Cardiol. 2010;31:1244-1248.

Walker Pg, et al. Semiautomated method for noise reduction and background phase error correction in mr phase velocity data. J Magn Reson Imaging. 1993;3:521-530.

Wetzel S, et al. In vivo assessment and visualization of intracranial arterial hemodynamics with flow-sensitized 4d mr imaging at 3t. AJNR Am J Neuroradiol. 2007;28:433-438.

PCT International Search Report and Written Opinion, PCT/US2016/015639, dated Apr. 1, 2016, 9 pages.

Transesophageal echocardiographic correlates of thromboembolism in high-risk patients with nonvalvular atrial fibrillation. The stroke prevention in atrial fibrillation investigators committee on echocardiography. Ann Intern Med. 1998;128:639-647.

Predictors of thromboembolism in atrial fibrillation: Ii. Echocardiographic features of patients at risk. The stroke prevention in atrial fibrillation investigators. Ann Intern Med/ 1992;116:6-12.

(56) References Cited

OTHER PUBLICATIONS

Echocardiographic predictors of stroke in patients with atrial fibrillation: A prospective study of 1066 patients from 3 clinical trials. Arch Intern Med. 1998;158:1316-1320.

* cited by examiner

SYSTEM AND METHOD FOR MAPPING AND QUANTIFYING IN-VIVO BLOOD FLOW STASIS

CROSS-REFERENCE TO RELATED APPLICATIONS

This application represents the national stage entry of International Application PCT/US2016/015639 filed Jan. 29, 2016, which claims the benefit of U.S. Provisional Application 62/109,909 filed Jan. 30, 2015. The contents of this application are hereby incorporated by reference as if set forth in their entirety herein.

BACKGROUND OF THE INVENTION

The field of the invention is systems and methods for medical imaging. More particularly, the invention relates to systems and methods for mapping and quantifying in-vivo blood flow stasis using medical imaging modalities, such as magnetic resonance imaging (MRI) and Doppler ultrasound.

Atrial fibrillation (AF) is a common cardiac arrhythmia and affects 33.5 million patients worldwide. It is associated with an increased risk of thrombus formation within the left atrial (LA) cavity. This increased risk is a major contributing factor to embolic stroke, the most serious complication of AF. Currently, an AF patient's annual stroke risk is estimated based on clinical risk models such as CHA2DS2-VASc scores. But, these scores have limited predictive accuracy (e.g., with C-statistics in the range of 0.55-0.67) because they are based on upstream clinical factors—such as age, gender, and diabetes—rather than individual physiologic factors implicating LA thrombus formation. MRI and Doppler echocardiography studies have shown that the increased risk of thrombus formation in AF patients may be related to flow abnormalities in the left atrium. This increased risk is because decreased blood flow velocity causes stasis, which increases the risk of blood clotting, and therefore stroke.

In light of the foregoing, it would be desirable to provide a system and method for mapping and quantifying in-vivo blood flow stasis.

SUMMARY OF THE INVENTION

The present invention overcomes the aforementioned drawbacks by providing a method for producing an image that depicts blood flow stasis using a medical imaging system. The method includes providing a time series of images that was acquired with the medical imaging system. The time series of images may include three-dimensional (3D) image volumes or two-dimensional (2D) image slices. The time series of images contains flow velocity information at voxel locations in a 3D volume. A one or more regions-of-interest are then segmented from each images in the time series of images. A velocity magnitude is calculated for each voxel in each region-of-interest, and a flow stasis volume is produced. The flow stasis volume is produced by computing a relative stasis value for each voxel location in each region-of-interest by determining, at a given voxel location, a number of time frames in the time series of images having a velocity magnitude below a user-selected threshold value and normalizing the determined number of time frames at the given voxel location by a total number of time frames in the times series of images. An image that depicts blood flow stasis is then generated from the produced flow stasis volume.

As one example, generating the flow stasis image can include providing the produced flow stasis volume as a three-dimensional image that depicts blood flow stasis. As another example, generating the flow stasis image can include producing a flow stasis map by projecting the flow stasis volume onto a two-dimensional (2D) plane, and providing the flow stasis map as the image that depicts blood flow stasis.

It is another aspect of the invention that the flow stasis map can be color-coded to better visualize the location and severity of flow stasis. In some embodiments, the flow stasis map can be overlaid on an anatomical image of the subject at the same plane that the 3D flow stasis volume is projected onto when generating the flow stasis map.

It is yet another aspect of the invention that the flow stasis map can be further processed or analyzed. As one example, the flow stasis map can be further processed to calculate the mean or median of the flow stasis distribution or to assess high-risk regions.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIGS. 5A-5B depicts the results of a sensitivity analysis for the identification of LA stasis and LA peak velocity thresholds in an example study.

DETAILED DESCRIPTION OF THE INVENTION

Described here are systems and methods for generating quantitative flow stasis maps based on in-vivo data of blood flow velocities acquired using medical imaging techniques, which may include magnetic resonance imaging ("MRI") and Doppler echocardiography.

The systems and methods described here produce blood flow stasis maps to noninvasively visualize and quantify flow abnormalities. The systems and methods also overcome drawbacks of current flow diagnostic tools.

Figure 1:
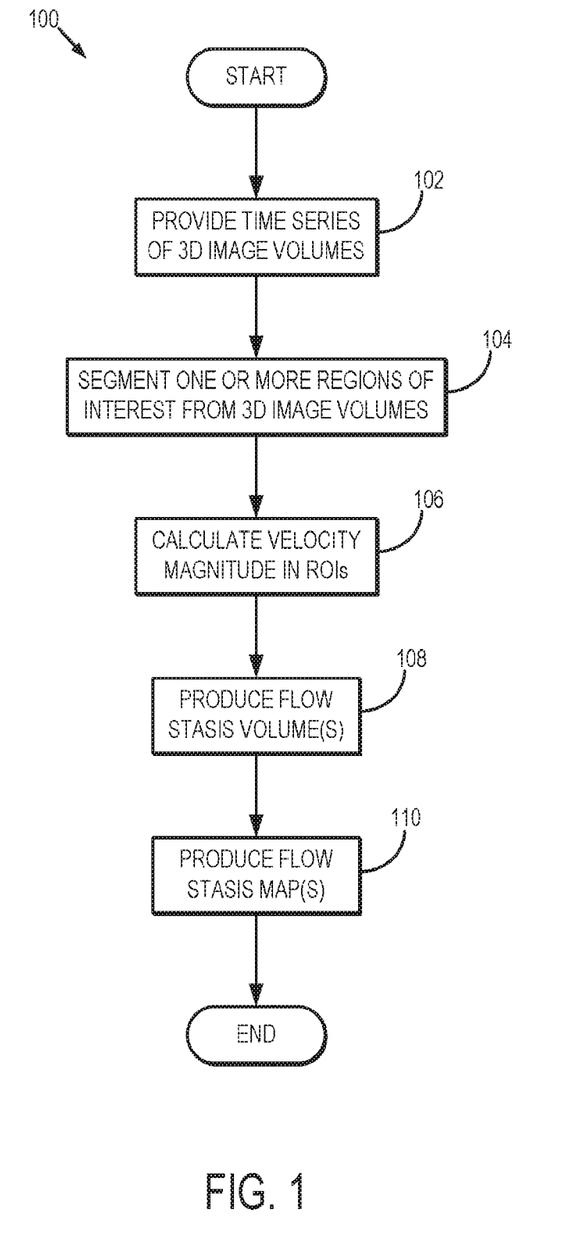
FIG. 1 is a flowchart setting forth the steps of an example of a method for producing an image that depicts blood flow stasis.

Referring now to FIG. 1, a flow chart is provided to illustrate an example of a method 100 for generating a blood flow stasis map in accordance with some embodiments of the present invention. In step 102, a time series of three-dimensional (3D) image volumes is provided. In other embodiments, a time series of two-dimensional (2D) image slices can alternatively be provided. These images can be acquired with an MRI system; an ultrasound system, such as an ultrasound system configured to perform Doppler echocardiography; or other medical imaging systems or instruments used to measure flow velocities. In general, the time series of 3D image volumes depicts the same 3D volume at a plurality of different time frames. The time series of 3D image volumes contains flow velocity information at voxel locations in this 3D volume.

In step 104, the 3D image volumes are segmented into regions-of-interest. As one example, the regions-of-interest can be associated with the left atrium ("LA"), the left atrial appendage ("LAA"), or other parts of a human body. In step 106, velocity magnitudes are calculated for each voxel in the regions-of-interest using the data provided in step 102.

As one example, 4-dimensional (4D) flow MRI data covering the entire left atrium (LA) can be provided, from which one or more regions-of-interest can be segmented. For instance, a region-of-interest associated with the LA can be segmented from each 3D image volume contained in the 4D flow MRI data. 4D flow MRI data provides information on three-directional blood flow velocities (vx(t), vy(t), vz(t)). In cardiac imaging applications, t can be the time after the peak of R-wave, and the blood flow velocities can be provided over the cardiac cycle within the entire LA. As described above, the flow data is segmented into regions-of-interest, which may also be referred to as 3D segmentation masks. These masks can then be used to isolate the velocity data in the one or more regions-of-interest, such as the LA volume. Flow distributions in the one or more regions-of-interest can be analyzed by calculating velocity magnitudes (v(t)= $\sqrt{v_x(t)^2+v_y(t)^2+v_z(t)^2}$ for all voxels inside the segmented regions-of-interest for all time frames.

In step 108, a flow stasis volume is produced based on the velocity magnitudes compared with a threshold value. As one example, for each voxel inside a segmented region-of-interest, the relative amount of flow stasis, $r_{stasis}$ (in percent), can be computed. The relative flow stasis can be calculated by determining the number of cardiac time frames (or 3D image volumes), $n_{stasis}$, with velocities below a threshold (e.g., 0.02-0.2 m/s) normalized by the total number of cardiac time frames (or 3D image volumes), $N_{tot}$, $$r_{stasis} = \frac{n_{stasis}}{N_{tot}} \times 100. \quad (1)$$

To intuitively visualize the relative flow stasis in the entire region-of-interest (e.g., the LA) for a given subject, flow stasis maps can be generated by projecting the relative flow stasis onto a 2D plane transecting the region-of-interest, as indicated at step 110. The resulting maps can be generated along any user selected viewing orientation.

In one example, the flow stasis map can be color-coded for intuitively identifying regions with low or high stasis. In another example, the flow stasis maps can be overlaid on an anatomic MRI image of the same plane corresponding to the projection through the 3D volume that is associated with the flow stasis map. Overlaying the flow stasis maps on an anatomical image in this manner can improve the anatomic orientation of the flow stasis maps.

In some embodiments, the flow stasis maps can be further processed or analyzed. For example, high-risk regions can be assessed by identifying voxels above stasis thresholds (e.g. when $r_{stasis}$>90%). As another example, regions with high-risk flow shown in color-coded stasis maps can be examined to better assess those regions. As still another example, the fraction of the LA/LAA volumes (or between other regions-of-interest) having high relative stasis can be calculated. In addition, flow stasis can be quantified by calculating mean and median relative stasis in the entire region-of-interest or in user-selected regions-of-interest, such as left atrial appendage. A 3D map of LA stasis can be generated by following the above steps without then projecting the relative stasis values onto a 2D plane.

In addition to the flow stasis maps, other images and maps can be generated to provide additional visualization of the LA. As one example, for each voxel inside the segmented LA, the maximum velocity within the cardiac cycle can be extracted. The maximum intensity projection ("MIP") over all of these maximum velocity values can then be calculated, resulting in a four-dimensional MIP of LA peak velocities. As another example, to quantify regional difference in timing of high LA flow velocities with respect to the beginning of the cardiac cycle, the time-to-peak ("TTP") velocity for each voxel in the segmented LA can be determined. TTP maps can then be generated by projecting the mean TTP onto a 2D plane.

Based on the flow stasis maps and the additional maps mentioned above, global stasis and TTP for the entire LA can be calculated by averaging over all LA voxels. The overall peak LA velocity can be calculated as the average over the top peak velocity threshold percentage of all LA velocities.

Figures 2A, 2B, 2C, 2D:
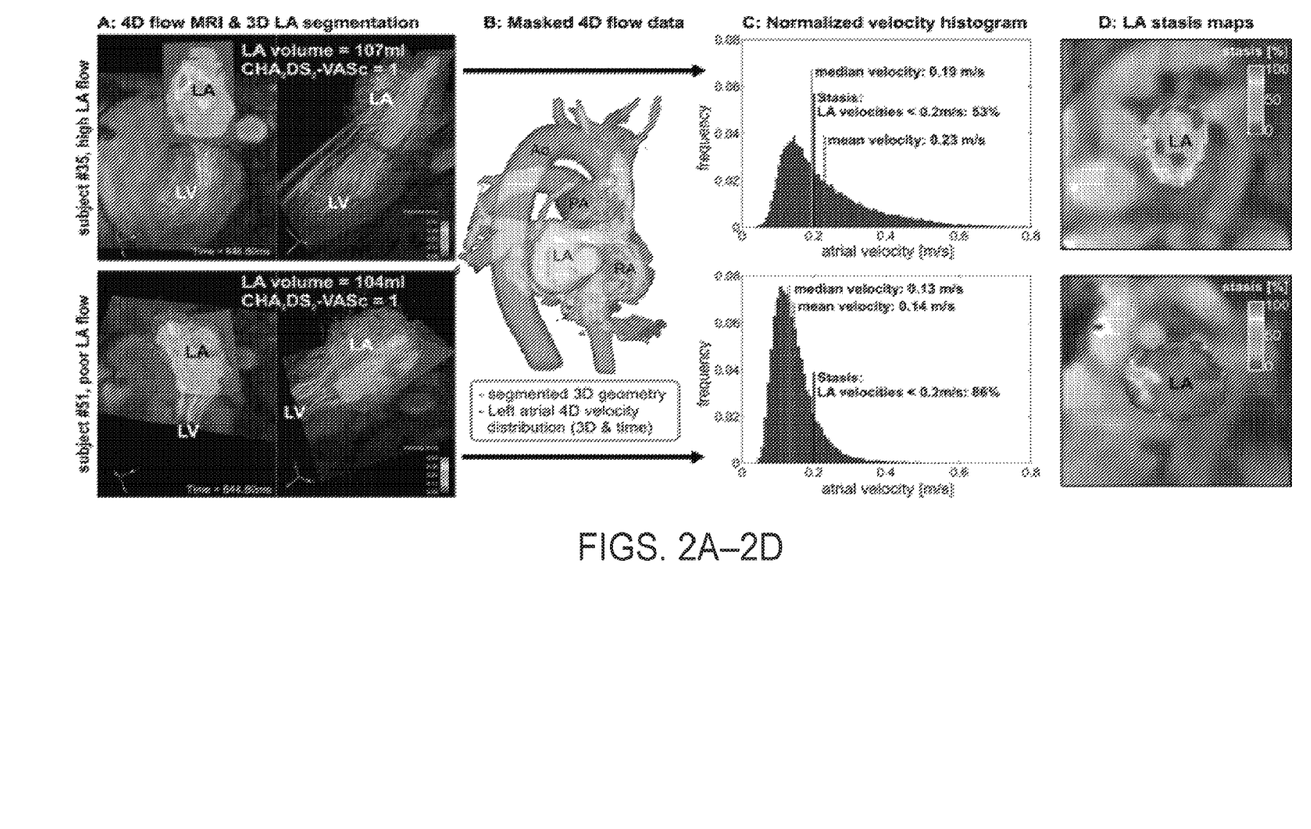
FIGS. 2A-2D illustrate an example that shows physiological information that can be derived from distribution of flow velocities and flow stasis for two different subjects.

As one example of the disconnect between clinical risk scores and quantified blood flow stasis, FIGS. 2A-2D illustrate examples in which the LA flow data and stasis maps of two AF patients in the pilot study are significantly different, even though the two patients have identical, low clinical risk scores (CHA2DS2–VASc=1). For both patients, 4D flow MRI was used to measure and visualize time-resolved 3D blood flow velocities in the LA and left ventricle (FIG. 2A). 3D segmentation (FIG. 2B) was used to isolate LA velocities. Velocity histograms were generated to quantify the LA flow velocity distributions of LA voxels (FIG. 2C). Here, the total number of data points used in computing histograms was the same across subjects. Flow stasis maps (FIG. 2D) were generated for intuitively visualizing stasis in the entire LA. For each LA voxel, the relative stasis (in %) was calculated as the percentage of time frames with velocities less than 0.2 m/s. Stasis maps were generated by projecting relative stasis onto a plane transecting the LA, as described above. The maps can be color-coded to help identify LA regions of high stasis (e.g., by color-coding these regions with a red color) and heightened risk for thrombogenesis. The subject illustrated on the bottom of FIG. 2D has substantially more regions of high stasis than the subject illustrated in the top of FIG. 2D, despite these two subjects having identical CHA2DS2-VASc scores.

Thus, the systems and methods described here can provide additional physiological information underlying AF based on data acquired with atrial 4D flow MRI. Velocity histograms and stasis maps can be used to distinguish distribution of velocities and stasis between subjects and assess their risks of thrombogenesis, even if those subjects have identical CHA2DS2-VASc scores. Similarly, other quantitative indices of LA flow, such as mean and median velocity and relative stasis as shown in FIG. 2C, differed substantially between subjects and can be used to assess the risks of thrombogenesis.

The systems and methods of generating flow stasis maps was further tested in 100 subjects (30 controls, 70 patients with AF) and found to provide intuitive visualization of otherwise complex 4D flow MRI data and to detect significant differences in LA flow distribution and levels of stasis. Atrial 4D flow MRI data of the 100 subjects was evaluated with the systems and methods described here. Quantification of LA flow and stasis demonstrated impaired LA flow ($p<0.006$) and increased stasis ($p<0.003$) in AF patients compared to controls. This study corroborated the results in the pilot study. That is, the indices of LA hemodynamics, as described here, provide physiologic information beyond CHA2DS2-VASc scores, especially for patients with low scores.

Figure 3:
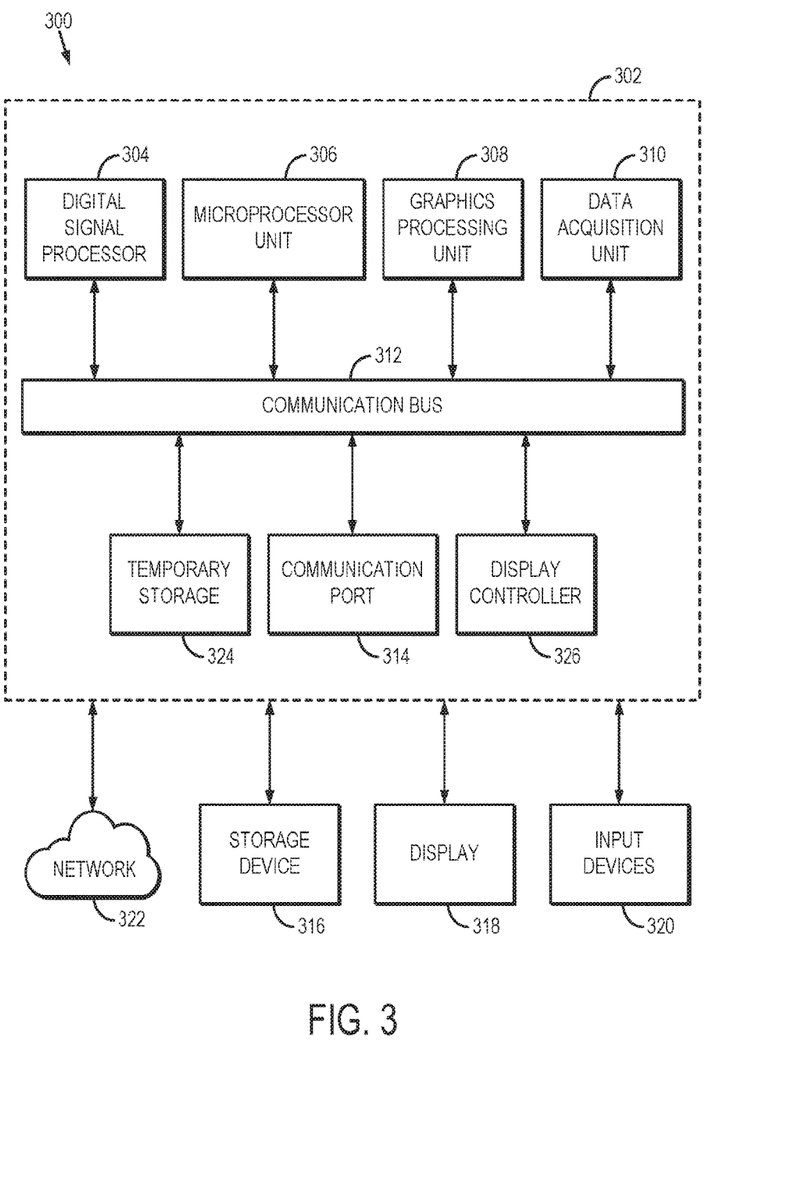
FIG. 3 is a block diagram of an example computer system that can be configured to implement the methods described herein.

Referring now to FIG. 3, a block diagram of an example computer system 300 that can be configured to compute and display flow stasis volumes or maps, as described above, is illustrated. The images from which the flow stasis volumes or maps are generated can be provided to the computer system 300 from the respective medical imaging systems, such as an MRI system or a Doppler ultrasound system, or from a data storage device, and are received in a processing unit 302.

In some embodiments, the processing unit 302 can include one or more processors. As an example, the processing unit 302 may include one or more of a digital signal processor ("DSP") 304, a microprocessor unit ("MPU") 306, and a graphics processing unit ("GPU") 308. The processing unit 302 can also include a data acquisition unit 310 that is configured to electronically receive data to be processed, which may include first and second medical images, image series, or image volumes. The DSP 304, MPU 306, GPU 308, and data acquisition unit 310 are all coupled to a communication bus 312. As an example, the communication bus 312 can be a group of wires, or a hardwire used for switching data between the peripherals or between any component in the processing unit 302.

The DSP 304 can be configured to receive and processes the medical images or medical image data received from the medical imaging system or storage device. The MPU 306 and GPU 308 can also be configured to process the medical images or medical image data in conjunction with the DSP 304. As an example, the MPU 306 can be configured to control the operation of components in the processing unit 302 and can include instructions to perform processing of the medical images or medical image data on the DSP 304. Also as an example, the GPU 308 can process image graphics.

In some embodiments, the DSP 304 can be configured to process the medical images or medical image data received by the processing unit 302 in accordance with the algorithms described above. Thus, the DSP 304 can be configured to segment images, select or otherwise identify regions-of-interest, calculate velocity magnitudes, and compute flow stasis volumes or maps.

The processing unit 302 preferably includes a communication port 314 in electronic communication with other devices, which may include a storage device 316, a display 318, and one or more input devices 320. Examples of an input device 320 include, but are not limited to, a keyboard, a mouse, and a touch screen through which a user can provide an input.

The storage device 316 is configured to store images, whether provided to or processed by the processing unit 302. The display 318 is used to display images, such as images that may be stored in the storage device 316, and other information. Thus, in some embodiments, the storage device 316 and the display 318 can be used for displaying images, including any generated flow stasis volumes or maps, and for outputting other information, such as data plots or other reports based on the quantitative flow stasis volumes or maps.

The processing unit 302 can also be in electronic communication with a network 322 to transmit and receive data, including magnetic resonance images, Doppler ultrasound images, and other information. The communication port 314 can also be coupled to the processing unit 302 through a switched central resource, for example the communication bus 312.

The processing unit 302 can also include a temporary storage 324 and a display controller 326. As an example, the temporary storage 324 can store temporary information. For instance, the temporary storage 324 can be a random access memory.

Example: Left Atrial 4-Dimensional Flow Magnetic Resonance Imaging Stasis and Velocity Mapping in Patients with Atrial Fibrillation In an example study, the potential of anatomic maps of LA stasis, peak velocity, and TTP velocity for the characterization of LA volume and flow, all derived from a single 4D flow MRI scan, was assessed.

Study Cohort.

A total of 111 subjects were included in the study (81 patients with AF and 30 healthy controls). Atrial fibrillation patients included 42 subjects with a history of AF and in sinus rhythm during MRI (AF-sinus; age, 62±11 years; 13 females) and 39 AF patients who were in AF at the time of imaging (AF-afib; age, 66±11 years; 11 females). In addition, 10 young healthy volunteers (HVs; age, 24±2 years; 4 females) and 20 age-appropriate controls (age, 59±7 years; 7 females) were included.

Magnetic Resonance Imaging.

All MRI examinations were performed on 1.5 T and 3 T MRI systems. All patients underwent standard-of-care cardiac MRI including retrospectively electrocardiogram (ECG)-gated time-resolved (CINE) balanced steady-state free precession imaging in 4-chamber, 2-chamber, and short-axis orientation of the left ventricle to evaluate left ventricular ejection fraction (LVEF). In addition, prospectively ECG-gated time-resolved 3D phase-contrast (PC) MRI with 3-directional velocity encoding (4D flow MRI) was employed to measure in vivo 3D blood flow velocities in the LA. Four-dimensional flow MRI data were acquired during free breathing using navigator gating of the diaphragm motion.[18,22] Further 4D flow MRI pulse sequence parameters were as follows: flip angle, 7 degrees; spatial resolution, 2.5-3.0 2.5-3.0×3.0-4.0 mm; temporal resolution, 37.6-41.6 milliseconds, imaging acceleration (generalized autocalibrating partially parallel acquisitions technique) with a reduction factor of R=2; total acquisition time of 10 to 20 minutes depending on heart rate and navigator efficiency; and velocity sensitivity of 100 to 150 cm/s. If Gd-contrast administration and contrast-enhanced magnetic resonance angiography (MRA) was part of the standard-of-care imaging protocol, 4D flow data was performed at the end of the MRI examination (i.e., 10-15 minutes after Gd injection). In case of contrast agent administration, the flip angle was adjusted to 15 degrees account for different blood T1.

4D Flow MRI Data Analysis.

Atrial stasis maps, peak LA velocity 4D MIPs, and TTP maps were generated as described above. All data were analyzed using a range of different velocity thresholds ($v_{stasis\_thresh}$=0.02-0.2 m/s in 0.02 m/s steps and $v_{peakvel\_thresh}$=1%-10% in 1% steps) to assess their influence on LA flow parameters and differences in LA flow dynamics between groups (young and older controls, AF-sinus, AF-afib). For each group, a Shapiro-Wilk test was used to determine if parameters were normally distributed. To compare parameters among the 4 groups, 1-way analysis of variance (Gaussian distribution) or Kruskal-Wallis (non-Gaussian distribution) was used. If these tests determined that a parameter was significantly different among groups (P<0.05), multiple comparisons between groups were performed using independent sample t-tests (Gaussian distribution) or Mann-Whitney U tests (non-Gaussian distribution). Bonferroni correction was used to adjust for multiple comparisons, and differences were considered significant for P<0.0125.

Left Atrial Stasis, Peak Velocity, and TTP Maps.

Figures 4A, 4B, 4C, 4D:
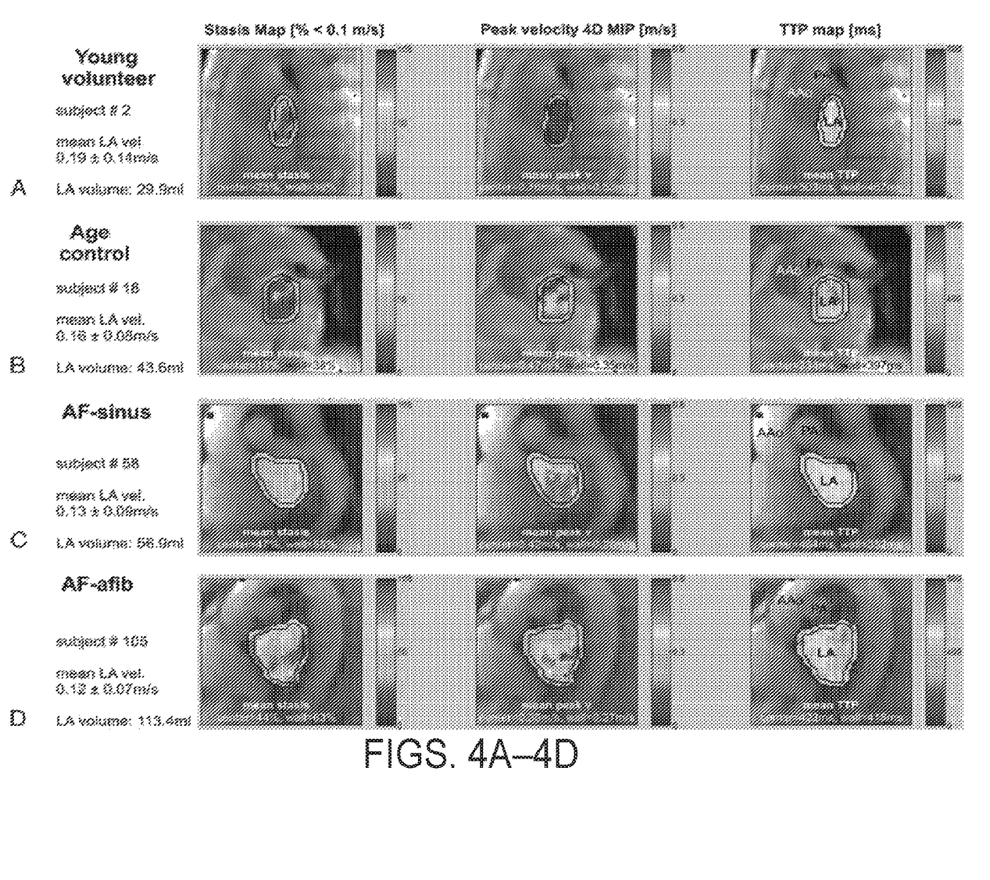
FIGS. 4A-4D show maps of LA flow parameters superimposed on the underlying anatomic 4D flow MRI data in oblique sagittal orientation. The individual images show stasis maps for a velocity threshold of 0.1 m/s (left column), peak velocity MIPs (4D, mid column), and TTP velocity maps (right column) in 4 subjects representing each of the subgroups in an example study. Areas for the analysis of regional flow dynamics (LA center and LA wall) are delineated, and the resulting regional LA stasis, peak velocities, and TTP are listed below each map. AAo indicates ascending aorta; PA, pulmonary artery.

Examples of LA flow parameter maps (stasis, peak velocity, TTP) for 4 representative subjects of each cohort are shown in FIG. 4. Four-dimensional flowMRI in a young HV (FIG. 4A) revealed high-peak velocities throughout the LA and lowest stasis compared with the 3 subjects from other groups. In all subjects, LA stasis based on a velocity threshold of 0.1 m/s showed an inhomogeneous pattern and was higher adjacent to the LA wall compared with the central region of the LA, which was confirmed by regional LA stasis quantification (see mean stasis for LA center and LA wall below individual maps).

The age-appropriate control subject (FIG. 4B) showed similar regional LA stasis patterns but considerably reduced LA peak velocities in both LA regions (average reduction by 38% and 34%, respectively). Atrial fibrillation patients (FIG. 4C and FIG. 4D) showed higher stasis throughout the LA (particularly adjacent to the LA wall) and lower and more heterogeneous distribution of LA peak velocities (specifically for AF-afib, FIG. 4D) compared with control subjects. Time-to-peak did not show consistent differences among groups.

Sensitivity Analysis: Identification of LA Stasis and LA Peak Velocity Thresholds.

Figure 5A:
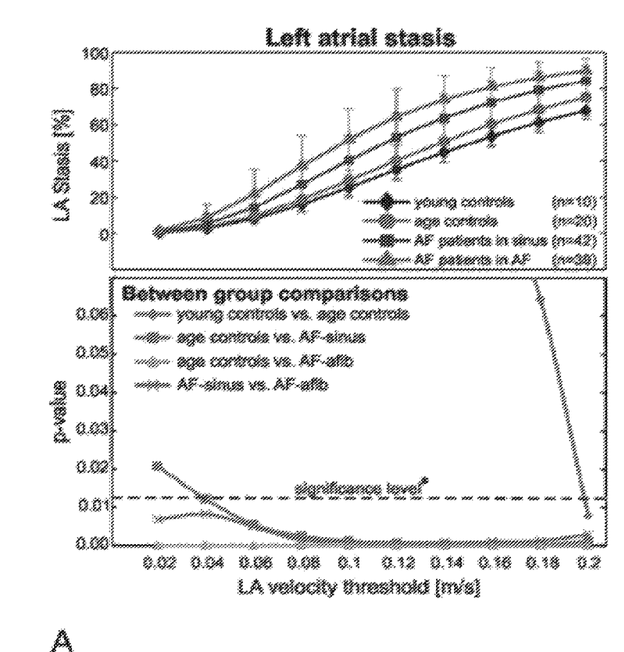
FIG. 5A shows LA stasis (top) as a function of the LA velocity threshold (% LA velocities<LA velocity threshold, $v_{stasis\_thresh}$) for all 4 groups (young volunteers, age-appropriate controls, AF-sinus, AF-afib). Corresponding P-values for pairwise comparisons of LA stasis between groups are shown below. FIG. SB shows peak LA velocities (top) for different thresholds (% of top LA velocities, $v_{peakvel\_thresh}$) and P-values for between group comparisons (bottom). The individual data points represent averaged over all subjects in each group. Error bars indicate inter-individual standard deviations of LA flow metrics.

FIG. 5 shows the results of the analysis of different thresholds for global LA stasis and peak velocity quantification. Except for young versus age-appropriate controls, LA stasis (FIG. SA) was significantly different between each of the groups (age matched controls, AF-sinus, AF-afib) for $v_{stasis\_thresh}$ 0.04 m/s or greater. Left atrial stasis could robustly differentiate between these groups for a wide range of velocity thresholds (P≤0.001 for $v_{stasis\_thresh}$ ranging from 0.10 to 0.18 m/s).

Figure 5B:
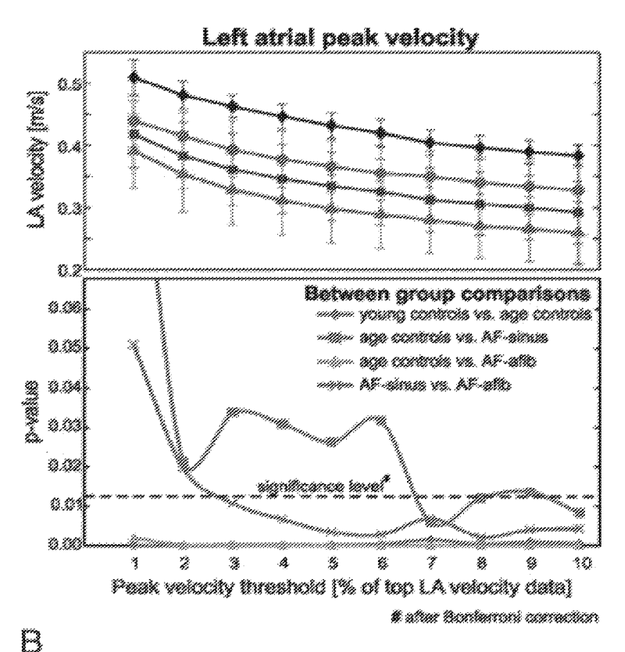

Findings for LA peak velocities are shown in FIG. 5B. Significant differences (P<0.0125) between each of the groups were found for a wide range of thresholds $v_{peakvel\_thresh}$ 3% or greater (except for AF-sinus versus age-appropriate controls). For further analysis of global LA stasis and peak velocity, $v_{stasis\_thresh}$ of 0.1 m/s and $v_{peakvel\_thresh}$ of 5% were chosen, respectively.

The present invention has been described in terms of one or more preferred embodiments, and it should be appreciated that many equivalents, alternatives, variations, and modifications, aside from those expressly stated, are possible and within the scope of the invention.

What is claimed is:

1. A method for producing an image that depicts blood flow stasis using a medical imaging system, the steps of the method comprising:
   (a) providing a time series of images acquired with the medical imaging system, the time series of images containing flow velocity information at voxel locations in a three-dimensional volume;
   (b) segmenting at least one region-of-interest from each image in the time series of images;
   (c) calculating a velocity magnitude for each voxel in each region-of-interest;
   (d) producing a flow stasis volume by computing a relative stasis value for each voxel location in each region-of-interest by determining, at a given voxel location, a number of time frames in the time series of images having a velocity magnitude below a user-selected threshold value and normalizing the determined number of time frames at the given voxel location by a total number of time frames in the times series of images; and
   (e) generating an image that depicts blood flow stasis from the produced flow stasis volume.

2. The method as recited in claim 1, wherein step (e) includes providing the produced flow stasis volume as a three-dimensional image that depicts blood flow stasis.

3. The method as recited in claim 1, wherein step (e) includes producing a flow stasis map by projecting the flow stasis volume onto a two-dimensional (2D) plane, and providing the flow stasis map as the image that depicts blood flow stasis.

4. The method as recited in claim 1, wherein the time series of images provided in step (a) is a time series of three-dimensional (3D) image volumes.

5. The method as recited in claim 1, wherein the time series of images provided in step (a) is a time series of two-dimensional (2D) image slices.

6. The method as recited in claim 1, wherein the medical imaging system is a magnetic resonance imaging (MRI) system.

7. The method as recited in claim 1, wherein the medical imaging system is an ultrasound system.

8. The method as recited in claim 1, wherein the user-selected threshold value is in a range of about 0.02 to 0.2 meters per second.

9. The method as recited in claim 1, wherein the user-selected threshold value is equal to or greater than about 0.04 meters per second.

* * * * *